United States Patent
Um et al.

(10) Patent No.: US 10,435,426 B2
(45) Date of Patent: Oct. 8, 2019

(54) METHOD FOR SEPARATION OF ACIDS AND SUGARS TO REDUCE ENERGY CONSUMPTION

(71) Applicant: KOREA INSTITUTE OF SCIENCE AND TECHNOLOGY, Seoul (KR)

(72) Inventors: Youngsoon Um, Seoul (KR); Kyung Min Lee, Seoul (KR); Sun-Mi Lee, Seoul (KR); Hong Gon Kim, Seoul (KR); Gyeongtaek Gong, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 16/198,017

(22) Filed: Nov. 21, 2018

(65) Prior Publication Data

US 2019/0161511 A1    May 30, 2019

(30) Foreign Application Priority Data

Nov. 28, 2017   (KR) .................. 10-2017-0160396

(51) Int. Cl.
| | |
|---|---|
| B01D 61/44 | (2006.01) |
| C07H 1/06 | (2006.01) |
| C07H 3/02 | (2006.01) |
| C12P 7/06 | (2006.01) |
| C10L 1/02 | (2006.01) |
| C25B 9/08 | (2006.01) |
| C25B 3/00 | (2006.01) |

(52) U.S. Cl.
CPC ............. *C07H 1/06* (2013.01); *C07H 3/02* (2013.01); *C10L 1/02* (2013.01); *C12P 7/06* (2013.01); *C25B 3/00* (2013.01); *C25B 9/08* (2013.01); *C10L 2200/0469* (2013.01); *C10L 2290/26* (2013.01); *C10L 2290/38* (2013.01); *C10L 2290/548* (2013.01)

(58) Field of Classification Search
CPC .... C07H 1/06; C07H 3/02; C25B 3/00; C25B 9/08; C10L 1/02; C10L 2290/38; C10L 2290/26; C10L 2200/0469; C10L 2290/548; C12P 7/06
See application file for complete search history.

(56) References Cited

U.S. PATENT DOCUMENTS

| | | | | |
|---|---|---|---|---|
| 4,923,611 | A | * | 5/1990 | Hanada ................. C08J 5/2243 210/500.42 |
| 5,820,687 | A | | 10/1998 | Farone et al. |
| 2014/0318969 | A1 | * | 10/2014 | Medoff ................. B01J 19/085 204/540 |

FOREIGN PATENT DOCUMENTS

| | | | | |
|---|---|---|---|---|
| DE | 19849924 A1 | * | 5/2000 | ........... B01D 61/445 |
| JP | 2009-022180 A | | 2/2009 | |

(Continued)

*Primary Examiner* — Arun S Phasge
(74) *Attorney, Agent, or Firm* — Rabin & Berdo, P.C.

(57) ABSTRACT

The present disclosure relates to a method for separating sugars and acids with reduced energy consumption, including a step of diffusively dialyzing a first acid hydrolysate obtained by saccharifying biomass with an acid solution, thereby preparing a second acid hydrolysate wherein the concentration of the acid solution contained in the acid hydrolysate is decreased; and a step of electrolyzing the second acid hydrolysate, thereby separating sugars from the acid solution, which is advantageous in that less energy is consumed, the separated acid solution can be recycled directly without further treatment due to high concentration and loss of sugars can be minimized.

13 Claims, 10 Drawing Sheets

(56) References Cited

FOREIGN PATENT DOCUMENTS

WO     WO-2015127531 A1 *   9/2015   .......... B01D 61/422
WO     WO 2016/047979 A1     3/2016

* cited by examiner

METHOD FOR SEPARATION OF ACIDS AND SUGARS TO REDUCE ENERGY CONSUMPTION

CROSS-REFERENCE TO RELATED APPLICATIONS

This application claims priority under 35 U.S.C. § 119 to Korean Patent Application No. 10-2017-0160396 filed on Nov. 28, 2017 in the Korean Intellectual Property Office, the disclosure of which is incorporated herein by reference in its entirety.

TECHNICAL FIELD

The present disclosure relates to a method for separating sugars and acids with reduced energy consumption, which is advantageous in that less energy is consumed, the separated acid solution can be recycled directly without further treatment due to high concentration and loss of sugars can be minimized.

BACKGROUND

As the production of biofuels capable of replacing petroleum increases in order to solve the problems of depletion of petroleum resources and global warming, the utilization of biomass is increasing gradually. The biofuels used as alternative energy are prepared by fermenting a hydrolysate obtained by treating biomass chemically or biologically.

The biomass that can be used includes edible and non-edible starches, grass, wood, seaweeds, organic waste resources (waste wood, agricultural and forestry byproducts, food byproducts, etc.), and so forth. Because the sugars contained in the biomass exist in the form of cellulose and hemicellulose, which are polysaccharides, they should be degraded into monosaccharides fermentable by microorganisms, such as hexoses or pentoses like glucose, xylose, arabinose, etc. For this, pretreatment and saccharification of the biomass are required.

The pretreatment is a process wherein the biomass is shredded into small pieces and treated with an acid or an alkali such that the structure in which cellulose, hemicellulose and lignin are strongly held together is disentangled and the cellulose and the hemicellulose are released at the molecular level.

The saccharification is a process wherein the cellulose and hemicellulose released at the molecular level in the pretreatment process, i.e., the polysaccharide structure, is saccharified (or hydrolyzed) using a high-concentration acid or a low-concentration acid and an enzyme to prepare a hydrolysate of monosaccharides.

When an alkali such as caustic soda, ammonia, etc. is used in the pretreatment process, the lignin is dissolved and the cellulose and hemicellulose are obtained in the form of solid cakes. After separating the sugar cakes, the monosaccharide components are obtained by conducting saccharification using an enzyme or an acid. However, the pretreatment method using an alkali has the problems in that the process is generally operated in batch mode under high-temperature and high-pressure conditions, a large amount of alkali liquid waste is generated and the solid cake causes troubles in the apparatus during a continuous process.

When sulfuric acid is used during the pretreatment and saccharification of biomass, a neutralization process is necessary for the following step. For example, when dilute sulfuric acid is used for the pretreatment and then the saccharification is performed using an enzyme, a neutralization process of adjusting the pH of the pretreated solution to a pH suitable for an enzymatic reaction is necessary. When the pretreatment is conducted using concentrated sulfuric acid and then the saccharification is performed using concentrated sulfuric acid, a neutralization process of separating (or removing) the sulfuric acid is necessary for fermentation of the saccharified hydrolysate by microorganisms in the following step. That is to say, the acid should be removed or the acid-sugar mixture should be neutralized for the following enzymatic saccharification or fermentation by microorganisms.

In order to remove sulfuric acid from a sugar-acid mixture prepared using sulfuric acid, a method of neutralizing with an alkali such as calcium hydroxide (Martinez et al., 2001) is mainly used. During this process, a large amount of gypsum is produced as waste and a significant amount of sugars are lost while separating the gypsum from the sugar solution. As another method of separating sugars and acids from the sugar-acid mixture obtained by pretreating with concentrated sulfuric acid and then performing saccharification, a continuous adsorptive separation method of using a simulated moving bed (SMB) is known. In this method, a number of chromatography (adsorption) columns selectively adsorbing and separating sugars or acids are installed and a valve and a pump are connected to each column to enable continuous sample injection and continuous product discharge, thereby continuously separating sugars and acids from the hydrolysate. However, it has problems in that the expensive chromatography (adsorption) column is used, operation is very complicated due to the complexity of apparatus configuration and, particularly, it is difficult to recycle the acid because the acid solution is diluted to about several % using water as a mobile phase fluid in chromatography column. In addition, because the adsorbent is swollen severely when it adsorbs the acid, the durability of the adsorbent worsens as the adsorption-desorption cycle is repeated.

In addition, a method of recovering the acid used in the pretreatment through an electrodialysis method has been reported recently. In the electrodialysis method, the separation is achieved based on the electrophoresis of ionic materials in the solution and the selective permeation of cations and anions through the ion-exchange membrane. A number of cation-exchange membranes and anion-exchange membranes are arranged alternatingly and the ionic materials in the solution can be separated by flowing direct current. Jaewon Lee et al. of Chungnam National University (Korea) recovered oxalic acid used for pretreatment from the hydrolysate using the electrodialysis method and Snyder et al. of Argonne National Laboratory (US) recovered sulfuric acid from the hydrolysate by filling an ionic resin in the diluate compartment of the electrodialysis apparatus. Although the acid used in the pretreatment could be separated from the hydrolysate using the electrodialysis method, the method is not applicable to high-concentration sulfuric acid.

In addition, the method based on electrodialysis is disadvantageous in that the system in which the anion- and cation-exchange membranes are arranged alternatingly is complicated and high-voltage electricity is required because the system becomes nonconducting as the ions are removed.

Therefore, in order to put the pretreatment of biomass using concentrated sulfuric acid or dilute sulfuric acid and saccharification into practical use, an economical method allowing effective recovery and recycling of sulfuric acid from the sugar-acid mixture without loss of sugars is necessary.

REFERENCES OF THE RELATED ART

Patent Document

U.S. Pat. No. 5,820,687.

SUMMARY

The present disclosure is directed to providing a method for separating sugars and acids with reduced energy consumption, which is advantageous in that less energy is consumed, the separated acid solution can be recycled directly without further treatment due to high concentration and loss of sugars can be minimized.

In an aspect, the method for separating sugars and acids with reduced energy consumption of the present disclosure may include: a step of diffusively dialyzing a first acid hydrolysate obtained by saccharifying biomass with an acid solution, thereby preparing a second acid hydrolysate wherein the concentration of the acid solution contained in the acid hydrolysate is decreased; and a step of electrolyzing the second acid hydrolysate, thereby separating sugars from the acid solution.

The diffusion dialysis may be performed using a diffusion dialyzer in which an acid hydrolysate inflow tank and a water tank are separated by an anion-exchange membrane and the reaction may be performed continuously as the first acid hydrolysate is added to the acid hydrolysate inflow tank and water is added to the water tank.

The electrolysis may be performed using an electrolyzer in which a cathode tank and an anode tank are separated by an anion-exchange membrane, the second acid hydrolysate wherein the concentration of the acid solution is decreased due to the diffusion dialysis may be added to the cathode tank and water or an acid solution may be added to the anode tank.

The concentration of the acid solution in the second acid hydrolysate may be decreased by 50-80% as compared to the concentration of the acid solution in the first acid hydrolysate due to the diffusion dialysis.

The concentration of the sugars separated by the electrolysis may be 0.1-200 g/L.

The content of the final acid solution present in the sugars separated by the electrolysis may be 1 wt % or lower.

The acid solution separated by the electrolysis may be used directly for the saccharification of biomass.

A biofuel may be produced by fermenting the sugars separated by the electrolysis.

Hydrogen gas and oxygen gas may be produced during the electrolysis.

The biomass may be grass biomass, wood biomass, starch biomass, seaweed biomass or organic waste.

The acid solution may be sulfuric acid.

The acid solution may be a strong acid aqueous solution having an acid concentration of 1-80%.

The separated sugar may be one or more selected from a group consisting of a polysaccharide selected from a group consisting of cellulose, hemicellulose, chitin, chitosan and derivatives thereof and a monosaccharide selected from a group consisting of glucose, xylose, galactose, fructose and arabinose.

In another aspect, the method for separating sugars and acids with reduced energy consumption of the present disclosure may include:

a step of diffusively dialyzing a first acid hydrolysate obtained by saccharifying biomass with an acid solution, at 23-25° C. using a diffusion dialyzer equipped with an ion-exchange membrane, thereby preparing a second acid hydrolysate wherein the concentration of the acid solution contained in the acid hydrolysate is decreased; and a step of electrolyzing the second acid hydrolysate using an electrolyzer by applying a voltage of 4-6 V at 38-42° C. when the concentration of the acid solution in the second acid hydrolysate is 7-8%, thereby separating sugars from the acid solution.

The number of the ion-exchange membrane in the step of preparing the second acid hydrolysate is not limited as long as 50-80% of the acid is removed.

The method for separating sugars and acids with reduced energy consumption of the present disclosure can remarkably reduce energy consumption and minimize the loss of sugars. In addition, because the selectively separated sulfuric acid can be recovered and recycled directly without further treatment, the productivity of biomass pretreatment and saccharification can be improved remarkably.

In addition, no waste is generated because the method of neutralizing or removing sulfuric acid using an alkali is not employed and the method of the present disclosure can be used in a fermentation process because sugar loss is minimized.

In addition, the produced high-purity hydrogen and oxygen may be collected and used as the energy source of a fuel cell or as a fuel, which is very economical because the consumed energy can be compensated for.

DETAILED DESCRIPTION OF EMBODIMENTS

The present disclosure relates to a method for separating sugars and acids with reduced energy consumption, which is advantageous in that less energy is consumed, the separated acid solution can be recycled directly without further treatment due to high concentration and loss of sugars can be minimized.

In the method of the present disclosure, electrolysis is performed after diffusion dialysis and energy consumption is reduced by 50-80% as compared to diffusion dialysis, electrolysis or diffusion dialysis performed after electrolysis.

Hereinafter, the present disclosure is described in more detail.

The method for separating sugars and acids with reduced energy consumption of the present disclosure includes: (A) a step of diffusively dialyzing a first acid hydrolysate obtained by saccharifying biomass with an acid solution, thereby preparing a second acid hydrolysate wherein the concentration of the acid solution contained in the acid hydrolysate is decreased; and (B) a step of electrolyzing the second acid hydrolysate, thereby separating sugars from the acid solution.

First, in the step (A), a first acid hydrolysate obtained by saccharifying biomass with an acid solution is diffusively dialyzed, thereby preparing a second acid hydrolysate wherein the concentration of the acid solution contained in the acid hydrolysate is decreased.

The present disclosure aims at selectively recovering the acid solution through the anion-exchange membrane according to the concentration gradient of the acid solution through diffusion dialysis with little energy consumption. The diffusion dialysis is advantageous in that it consumes little energy, the apparatus is simple, the operation is continuous and stable, system maintenance is simple and the cost of installation and maintenance is low. Accordingly, sugars and acids can be separated with reduced energy consumption if diffusion dialysis is performed before electrolysis.

Figure 1:
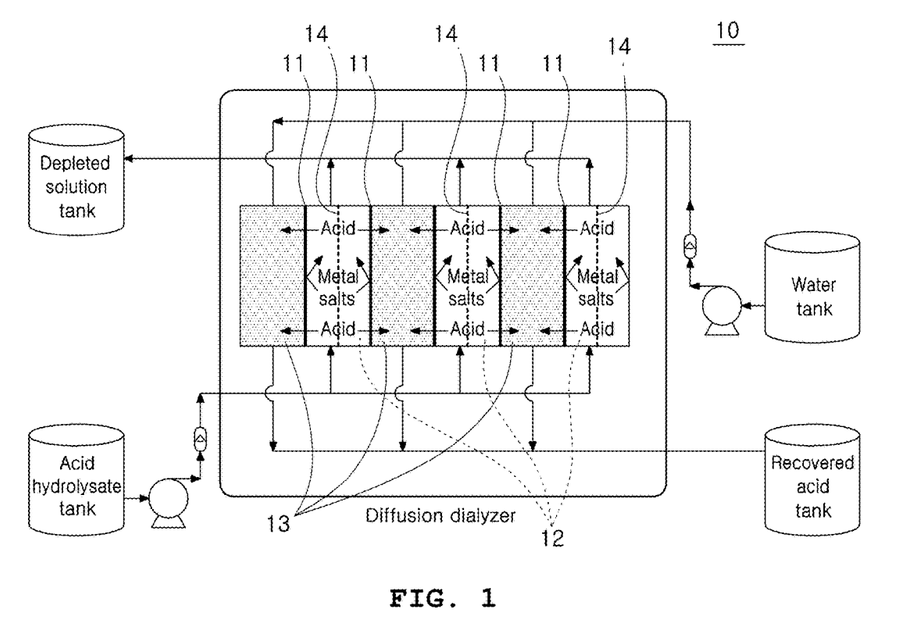
FIG. 1 shows diffusion dialysis according to an exemplary embodiment of the present disclosure.

A diffusion dialyzer for diffusively dialyzing the first acid hydrolysate is equipped with an acid hydrolysate inflow tank 12, a water tank 13 and a first anion-exchange membrane 11 separating the tanks, which are arranged alternatingly, as shown in FIG. 1. At the center of the acid hydrolysate inflow tank 12, specifically at the center of the acid hydrolysate inflow tank 12 equipped with the first anion-exchange membranes 11 on both sides, a mesh 14 is formed in the same direction as the first anion-exchange membrane 11. The mesh 14 allows the solution between the first anion-exchange membrane 11 and the first anion-exchange membrane 11 to be mixed to generate turbulence, rather than being bypassed, so that the boundary layer of the acid formed on the first anion-exchange membrane 11 is minimized and diffusion occurs more effectively. If the mesh 14 is not equipped, diffusion occurs insignificantly. The mesh size of the mesh 14 is 0.2-1 cm×0.2-1 cm. If the mesh size is smaller than the lower limit, the movement of the solution may be slow. And, if it is larger than the upper limit, the diffusion effect may not be achieved.

While the diffusion dialysis is performed as a first acid hydrolysate is added to the acid hydrolysate inflow tank 12 and an electrolyte (water) hydrolysate is added to the water tank 13, the acid solution contained in the acid hydrolysate is transferred from the acid hydrolysate inflow tank 12 to the water tank 13 and the concentration of the acid solution in the acid hydrolysate inflow tank 12 is decreased by 50-80%. As the acid in the acid hydrolysate inflow tank 12 is transferred to the water tank 13, the solution volume is decreased by about 5-10% and, as a result, the sugar concentration (%) is increased. The increased sugar concentration provides an additional effect of increasing the concentration of the fermentation product (biofuel and raw materials).

Specifically, the concentration of the acid solution in the first acid hydrolysate added to the acid hydrolysate inflow tank 12 is about 25-30%. As only the acid solution is selectively transferred through the anion-exchange membrane according to the concentration gradient through the diffusion dialysis, the concentration of the acid solution in the hydrolysate can be decreased to 7-15%. The water added to the water tank 13 decreases the concentration of the acid solution to 10-15%. Then, the diffusively dialyzed second hydrolysate is transferred to an electrolyzer for the next step.

The first acid hydrolysate is prepared by pretreating biomass with an acid solution and then saccharifying the pretreated biomass.

The first acid hydrolysate and the second acid hydrolysate of the present disclosure refer to solutions in which the acid solution and the saccharified sugar are mixed.

The acid solution is a strong acid aqueous solution with an acid concentration of 1-80%. There are two methods for preparing the acid hydrolysate depending on the acid concentration.

One is a method using concentrated sulfuric acid wherein biomass is pretreated with an acid solution having an acid concentration of 70-80% at 23-26° C. and then saccharification is performed at 60-80° C. by lowering the acid concentration to 25-30% by adding water. The other is a method using dilute sulfuric acid wherein biomass is pretreated with an acid solution having an acid concentration of 1-5% at 150-250° C. and 1-2 MPa and then saccharification is performed using an enzyme. When the dilute sulfuric acid method is used, if polysaccharides such as cellulose, etc. and monosaccharides such as glucose, etc. are present in the pretreated biomass, the mixed sugar and the acid may be separated before treating with the enzyme.

The biomass may be grass biomass, wood biomass, starch biomass, seaweed biomass or organic waste. The organic waste may include waste wood, agricultural and forestry byproduct, food byproduct, etc.

As the acid solution, one or more selected from a group consisting of sulfuric acid, sulfamic acid, citric acid, succinic acid, maleic acid and phthalic acid may be used. Specifically, sulfuric acid may be used because, unlike other acid solutions, sulfuric acid is inexpensive and use of high-concentration sulfuric acid enables pretreatment and saccharification of most of biomass including tough lignocellulosic biomass in short time and provides high saccharification efficiency.

The saccharified sugar may be one selected from a group consisting of a polysaccharide selected from a group consisting of cellulose, hemicellulose, chitin, chitosan and derivatives thereof; a monosaccharide selected from a group consisting of glucose, xylose, galactose, fructose, mannose and arabinose; and a dimer or an oligomer consisting of at least one monosaccharide selected from the group consisting of glucose, xylose, galactose, fructose, mannose and arabinose.

Next, in the step (B), the second acid hydrolysate is electrolyzed, thereby separating sugars and the acid solution and producing hydrogen gas and oxygen gas.

The present disclosure is also directed to providing an economical method capable of bioenergy and hydrogen energy at the same time by separating the acid solution into hydrogen gas and acid salts using the electrons generated by electrochemical water splitting, recovering the separated acid salts using the anion-exchange membrane and producing hydrogen gas additionally.

Figure 2:
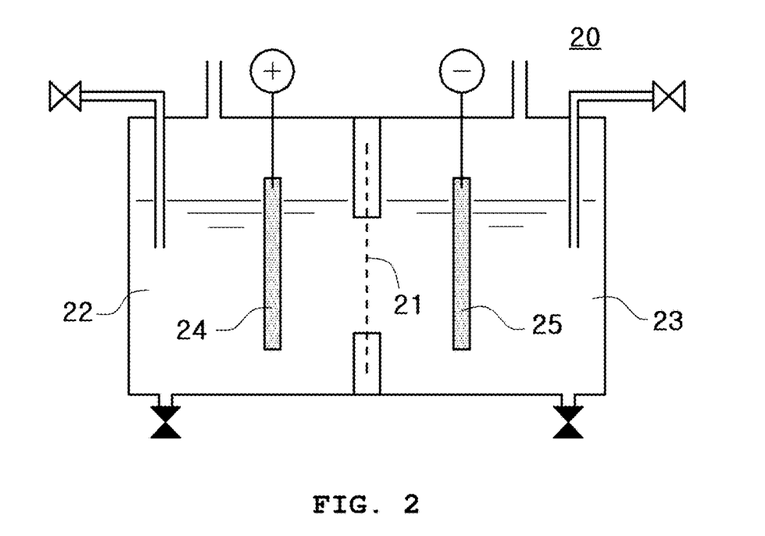
FIG. 2 shows an electrolyzer according to an exemplary embodiment of the present disclosure.

The electrolyzer for electrolyzing the second acid hydrolysate includes a cathode tank 23, an anode tank 22 and a second anion-exchange membrane 21 separating the tanks, as shown in FIG. 2. The second anion-exchange membrane 21 separating the tanks may be singular or plural. When it is plural, the cathode tank 23 and the anode tank 22 are also provided in plural numbers as shown in FIG. 1.

While electrolysis is performed as the second acid hydrolysate is added to the cathode tank 23 and an electrolyte (water or an acid solution) is added to the anode tank 22, the acid solution contained in the second acid hydrolysate is mostly transferred from the cathode tank 23 to the anode tank 22 and the acid solution is almost nonexistent and only sugars are present in the cathode tank 23. In addition, hydrogen gas is produced in the cathode tank 23 during the electrolysis. Specifically, if sulfuric acid is used as the acid solution, the sulfuric acid in the second acid hydrolysate filled in the cathode tank is ionized and exists in the form of hydrogen ion ($H^+$) and sulfate ion ($SO_4^{2-}$). When electricity is supplied, hydrogen ($H_2$) gas is generated on the surface of a cathode immersed in the cathode tank as the hydrogen ion ($H^+$) receives electrons and the sulfate ion ($SO_4^{2-}$) is transferred to the anode tank through the anion-exchange membrane.

Because 90 wt % or more, specifically 90-99 wt %, of the acid solution existing in the second acid hydrolysate prior to the electrolysis is removed, gypsum is hardly produced as a waste even after the sugars are neutralized for fermentation. As the amount of the gypsum produced is decreased, sugar loss caused by the adsorption of the gypsum is also decreased. If the acid neutralization and sugar separation are conducted through neutralization rather than through the electrolysis of the present disclosure, a large amount of gypsum is produced as the content of the acid solution in the sugars is higher, resulting in increased sugar loss.

On the surface of an anode immersed in the anode tank 22, water is split and oxygen ($O_2$) gas is generated. The hydrogen ion ($H^+$) generated through the water splitting is concerted to an acid as it encounters the acid ion transferred from the cathode tank (If the acid solution is sulfuric acid, it is concerted to sulfuric acid by encountering sulfate ion ($SO_4^{2-}$)). Specifically, when sulfuric acid is used as the acid solution, water is electrolyzed in the anode tank of the electrolyzer and, at the same time, the sulfate ion ($SO_4^{2-}$) in the cathode tank is transferred to the anode tank. As a result, sulfuric acid is separated from the cathode tank and is transferred to and concentrated in the anode tank. Accordingly, a hydrolysate with the sulfuric acid removed can be prepared in the cathode tank and sulfuric acid can be recovered from the anode tank for recycling for pretreatment and saccharification. Because water is consumed through electrolysis during this process, the sugars are concentrated in the cathode tank and the acids are concentrated in the anode tank.

The current applied to the electrolyzer is not limited as long as anions can be transferred through the anion-exchange membrane. Specifically, the current is maintained such that the current density per unit area of the anion-exchange membrane is 10-40 ASD, more specifically 20-30 ASD. If the current density is below the lower limit, the sugar-acid separation proceeds very slowly as compared to when it is within the above range. And, if the current density exceeds the upper limit, the anion-exchange membrane may be damaged easily or energy efficiency may decrease due to heat generation, etc. as compared to when it is within the above range.

It is not necessary to maintain the current density at the same value and constant-voltage or constant-current operation may be adopted, if necessary.

The voltage applied to the electrolyzer may be 1.23 V or higher, specifically a voltage selected from 2 to 33 V. If the voltage is below the lower limit, the hydrolysate may be denatured because a long time is required for the electrolysis or the electrolysis may not occur. And, if the voltage exceeds the upper limit, the anion-exchange membrane may be damaged easily or energy efficiency may decrease due to heat generation, etc.

Each of the anode 24 and the cathode 25 used for the anode tank 22 and the cathode tank 23 may be made of metal, precious metal or carbon. Specifically, both of the two electrodes may be made of platinum.

As the first and second anion-exchange membranes 11, 21 of the present disclosure, those allowing salt ions to be transferred through the anion-exchange membranes 11, 21 may be used. Specifically, a DSV, AFN, ACM or AFX anion-exchange membrane may be used. More specifically, a DSV anion-exchange membrane may be used. If cation-exchange membranes are used instead of the anion-exchange membranes 11, 21, acids and sugars may not be separated. And, if the cation-exchange membrane and the anion-exchange membrane are arranged alternatingly, separation time may increase and the efficiency of electrical energy may decrease as the resistance resulting from the electrode membranes increases and cations and anions are transferred at the same time.

Next, useful materials such as a biofuel, etc. are produced by fermenting the separated sugars.

The separated sugars are converted to a bioalcohol, which is a biofuel, by fermenting with microorganisms.

Because the separated sugars have 90% or more, specifically 90-99 wt %, of the acid solution existing in the second acid hydrolysate prior to the electrolysis removed, they may be fermented directly without neutralization with an alkali. Even when neutralization is performed, waste is hardly generated because the acid content is low and, therefore, sugar loss hardly occurs. In addition, the separated sugars may be used not only to prepare useful materials such as a biofuel, etc. but also to produce metabolites such as lactic acid, succinic acid, MSG, etc.

The microorganisms are not specially limited and may be common microorganisms used to useful materials such as the biofuel, etc.

In the present disclosure, the conditions are controlled such that the concentration of the separated sugars is 0.1-200 g/L, specifically 1-200 g/L, more specifically 10-200 g/L, more specifically 100-200 g/L. If the sugar concentration is below the lower limit, microorganisms cannot grow and, therefore, fermentation cannot be achieved. And, if the sugar concentration exceeds the upper limit, mixing for fermentation may be difficult.

In addition, if a step of diffusively dialyzing a first acid hydrolysate obtained by saccharifying biomass with an acid solution, at 23-25° C. using a diffusion dialyzer equipped with an ion-exchange membrane, thereby preparing a second acid hydrolysate wherein the concentration of the acid solution comprised in the acid hydrolysate is decreased and a step of electrolyzing the second acid hydrolysate using an electrolyzer by applying a voltage of 4-6 V at 38-42° C. when the concentration of the acid solution in the second acid hydrolysate is 7-8%, thereby separating sugars from the acid solution are performed, the separated sugars may be fermented with microorganisms to obtain not only bioethanol but also the industrially useful intermediate furfural.

Hereinafter, the present disclosure will be described in more detail through examples. However, the following examples are for illustrative purposes only and not intended to limit the scope of this disclosure.

Preparation Example 1. Number of Anion-Exchange Membranes of Diffusion Dialyzer

Because a large effective membrane area per unit volume and the concentration gradient of solutions across the membrane are of significant importance, a diffusion dialyzer was configured, by using a plurality of membranes in order to increase the membrane area, such that counter flow of each solution is possible in each channel compartmented by the ion-exchange membranes. The total area of the diffusion dialyzer was 10.5 cm×10.5 cm and the effect area for reaction with the ion-exchange membrane was 5 cm×5 cm. The distance between the ion-exchange membranes compartmented by a flow plate and a gasket was fixed to 0.23 cm (0.1 cm+0.03 cm+0.1 cm).

Prior to actually separating sugars and acids from an acid hydrolysate, each ion-exchange membrane of a continuous diffusion dialyzer was tested to check if a result similar to that of a batch reactor can be achieved. As described above, the area of the ion-exchange membrane plays an important role in recovering acids from the hydrolysate. Because the area inside the reactor increases with the area of the ion-exchange membrane, 3, 6, 9 and 13 sheets of the anion-exchange membrane were used to investigate the time to reach the steady state.

Figure 3:
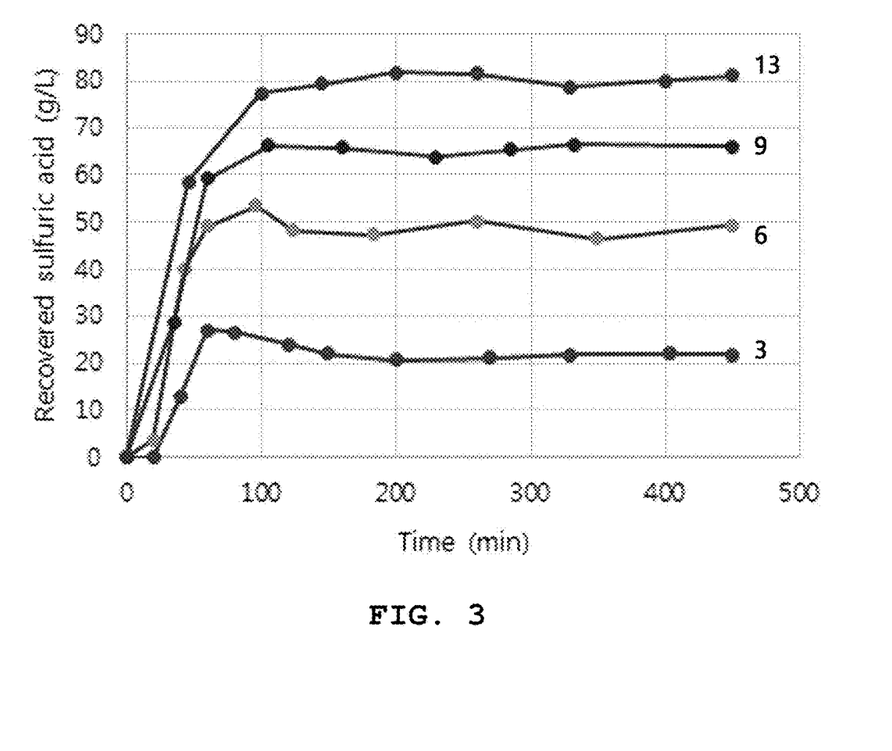
FIG. 3 shows the time to reach the steady state depending on the number of DSV ion-exchange membranes.

FIG. 3 shows the result of measuring the time to reach the steady state depending on the number (sheets) of DSV ion-exchange membranes. When a model hydrolysate (250 g/L sulfuric acid, 40 g/L glucose, 20 g/L xylose) was supplied from an acid hydrolysate inflow tank and distilled water was supplied from a water tank at the same rate of 1 mL/min and the transfer volume of sulfuric acid was measured after recovering the discharged solution, the time to reach the steady state was different but the removed volume of sulfuric acid was maintained constant after 240 minutes.

Preparation Example 2. Transfer of Acids and Sugars Depending on Anion-Exchange Membrane of Diffusion Dialyzer In order to find the optimum ion-exchange membrane for separating sugars and acids from the acid hydrolysate, the DSV membrane of Asahi Glass and the AFN and AFX membranes of Astom were used as the ion-exchange membrane of a continuous diffusion dialyzer. After supplying model hydrolysate (250 g/L sulfuric acid, 40 g/L glucose, 20 g/L xylose) from the acid hydrolysate inflow tank and distilled water from the water tank at a rate of 1 mL/min, the removal of sulfuric acid and the loss of sugars were measured.

Figure 4A:
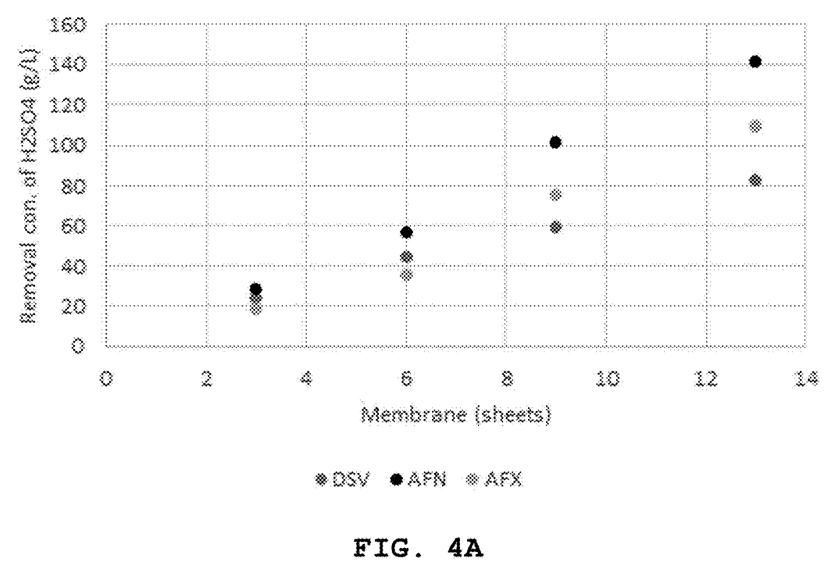
FIGS. 4A and 4B show the amount of removed sulfuric acid and sugar loss depending on the ion-exchange membrane used in a diffusion dialyzer.
Figure 4B:
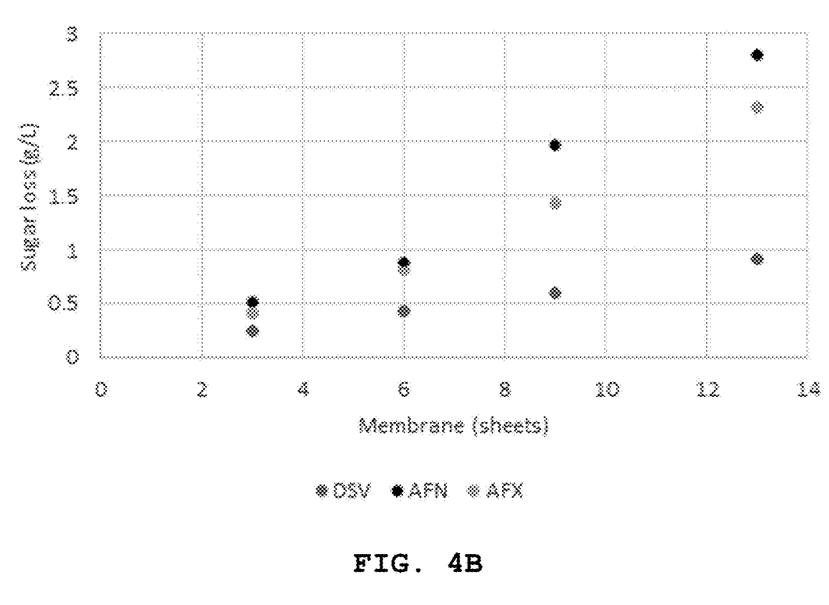

FIG. 4 shows the result of measuring the amount of removed sulfuric acid (a) and sugar loss (b) depending on the ion-exchange membrane used in the diffusion dialyzer.

As seen from FIGS. 4 (a) and (b), the amount of removed sulfuric acid was 141.20 g/L for AFN, 109.40 g/L for AFX and 82.71 g/L for DSV, when 13 sheets of the -exchange membrane were used.

And, the sugar loss was 2.80 g/L for AFN, 2.32 g/L for AFX and 0.92 g/L for DSV.

Through this, it was confirmed that the DSV ion-exchange membrane shows the least sugar loss.

Because the concentration of sulfuric acid of the acid hydrolysate was about 240 g/L, calibration curves were constructed based on the experimental result conducted to determine the number of ion-exchange membranes required to remove 240 g/L sulfuric acid with the ion-exchange membrane. The following equations were obtained.

$DSV: y=5.7917x+7.6916 (R^2=0.9981)$ $AFN: y=11.587x-7.9688 (R^2=0.9937)$ $AFX: y=9.4364x-13.337 (R^2=0.9828)$ [Equation 1]

From the above equations, it can be seen that, although the number of the ion-exchange membranes required to remove 240 g/L sulfuric acid is 21 sheets for AFN, 26 sheets for AFX and 40 sheets for DSV, sugar loss is about 2 times lower for DSV (2.6 g/L) than AFN (4.7 g/L) or AFX (4.9 g/L). Therefore, the following experiments were conducted using the DSV ion-exchange membrane.

Preparation Example 3. Transfer of Acids and Sugars Depending on Temperature of Diffusion Dialyzer Because temperature is an important factor for diffusion dialysis efficiency, the efficiency of removing acids from the acid hydrolysate was measured for different temperatures. Because the temperature at which DSV selected as the optimum ion-exchange membrane is 40° C., the efficiency of sulfuric acid transfer was compared at room temperature (25° C.) and 40° C.

A model hydrolysate (250 g/L sulfuric acid, 40 g/L glucose, 20 g/L xylose) was supplied from the acid hydrolysate inflow tank and distilled water was supplied from the water tank at a rate of 1 mL/min. As the ion-exchange membrane, DSV was used. The sulfuric acid removal amount and sugar loss were measured using 9, 18, 27 or 36 sheets of the ion-exchange membrane. All the experiments were conducted twice.

Figure 5A:
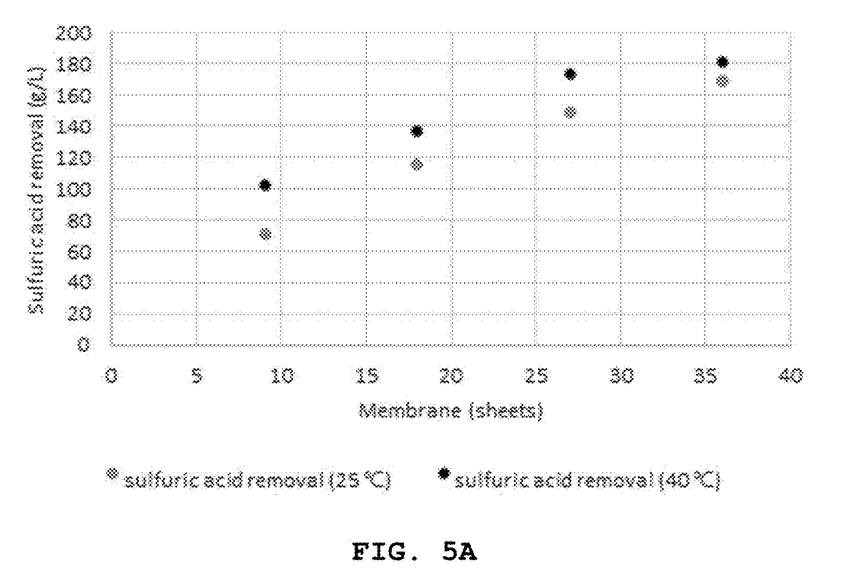
FIGS. 5A and 5B show the amount of removed sulfuric acid and sugar loss depending on temperature in a diffusion dialyzer.
Figure 5B:
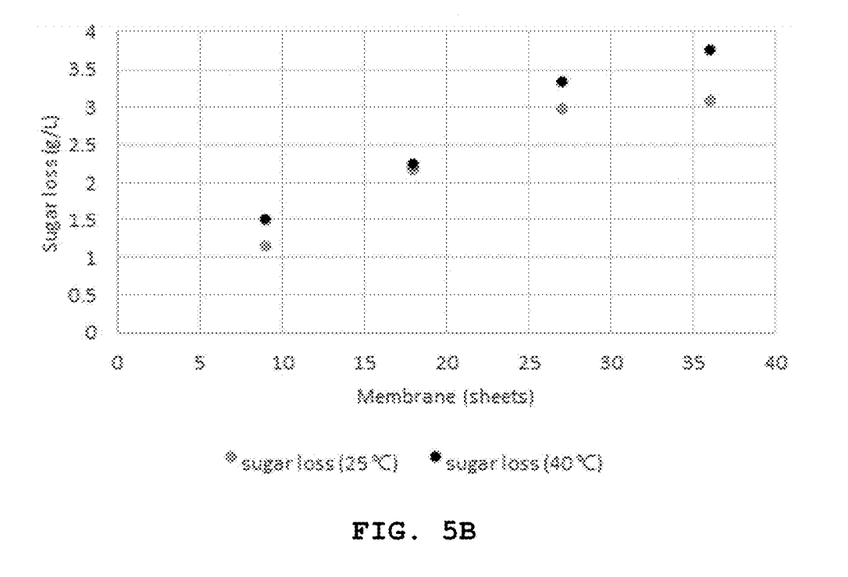

FIG. 5 shows the amount of removed sulfuric acid (a) and sugar loss (b) depending on the temperature of the diffusion dialyzer.

As seen from FIGS. 5 (a) and (b), when 9 sheets of the ion-exchange membrane were used, the removed amount of sulfuric acid was 1.45 times higher at 40° C. (102.55 g/L) than at 25° C. (70.91 g/L). When 18 and 27 sheets were used, the difference was decreased to 1.17 times (136.31 g/L and 115.89 g/L) and 1.16 times (173.27 g/L and 148.77 g/L). When 36 sheets were used, the removed amount was almost similar (181.15 g/L and 169.43 g/L).

Meanwhile, the sugar loss was 1.21 times higher at 40° C. (3.76 g/L) than at 25° C. (3.10 g/L) when the number of the ion-exchange membrane was 36 sheets.

Because it is important to minimize sugar loss when removing sulfuric acid from the acid hydrolysate as described above, the following experiments were conducted at room temperature (25° C.).

Control Example 1. Electrolysis of Model Hydrolysate after Diffusion Dialysis

A model hydrolysate (229.65 g/L sulfuric acid, 61.35 g/L glucose, 31.02 g/L xylose; model hydrolysate with a concentration similar to the actual hydrolysate used in Example 1) was supplied from the acid hydrolysate inflow tank and distilled water was supplied from the water tank at a rate of 1 mL/min. As the ion-exchange membrane, 36 sheets of DSV were used and the experiment was conducted at room temperature.

The acid remaining in the diffusively dialyzed hydrolysate (second hydrolysate) at a concentration of 7% was removed through electrolysis in the following experiment. The diffusively dialyzed hydrolysate is used as a cathode solution and the distilled water with the acid recovered is used as an anode solution. An Ir—Pt-coated MMO electrode was used as the electrode and ACM was used as the anion-exchange membrane. The distance between two sheets of the anion-exchange membrane was 0.7 cm. The total area of the reactor was 10.5 cm×10.5 cm and the area of the actual anion-exchange membrane and the electrode was 5 cm×5 cm.

The electrolysis was conducted by applying a current of 25 ASD and a voltage of 5 V and the operation was conducted at 40° C. or below to prevent the damage of the ion-exchange membrane. The experiment was conducted while circulating 200 mL of the solutions flown into the cathode and the anode at a rate of 65.0 mL/min.

Example 1. Electrolysis of Actual Hydrolysate after Diffusion Dialysis

An actual hydrolysate (pine biomass; 226.59 g/L sulfuric acid, 56.21 g/L glucose, 27.84 g/L xylose) was supplied from the acid hydrolysate inflow tank of the diffusion dialyzer and distilled water was supplied from the water tank at a rate of 1 mL/min, respectively. 36 sheets of DSV were used as the ion-exchange membrane and the experiment was conducted at room temperature.

The acid remaining in the diffusively dialyzed hydrolysate (second hydrolysate) at a concentration of 7% was removed through electrolysis in the following experiment. The diffusively dialyzed hydrolysate is used as a cathode solution and the distilled water with the acid recovered is used as an anode solution. An Ir—Pt-coated MMO electrode was used as the electrode and ACM was used as the anion-exchange membrane. The distance between two sheets of the anion-exchange membrane was 0.7 cm. The total area of the reactor was 10.5 cm×10.5 cm and the area of the actual anion-exchange membrane and the electrode was 5 cm×5 cm.

The electrolysis was conducted by applying a current of 25 ASD and a voltage of 5 V and the operation was conducted at 40° C. or below to prevent the damage of the ion-exchange membrane. The experiment was conducted while circulating 200 mL of the solutions flown into the cathode and the anode at a rate of 65.0 mL/min.

Test Examples

Test Example 1. Separation of Acids and Sugars Using Diffusion Dialyzers of Control Example 1 and Example 1

Figure 6A:
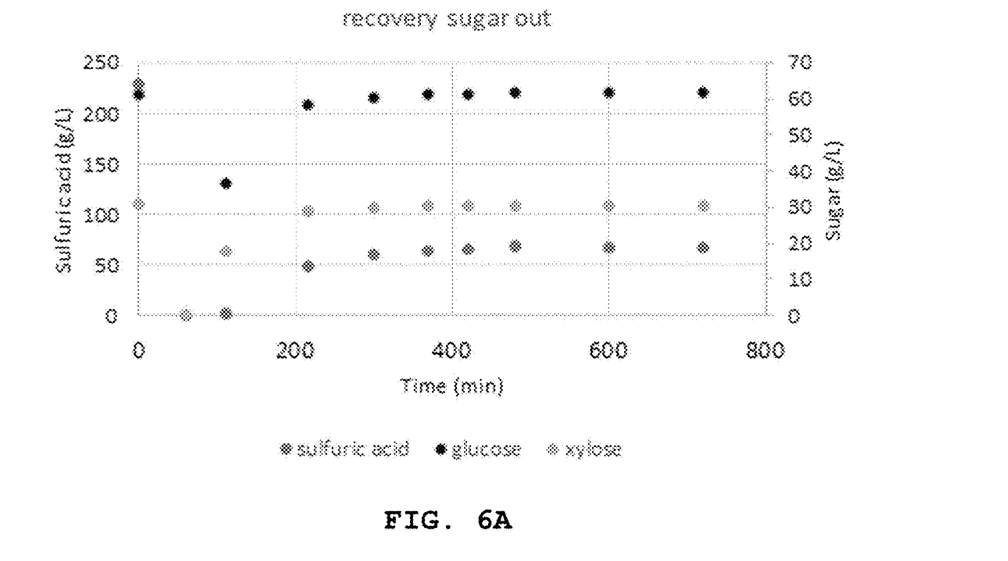
FIGS. 6A and 6B show the change in the transfer of sugars and acids from a model hydrolysate in a diffusion dialyzer of Control Example 1.
Figure 6B:
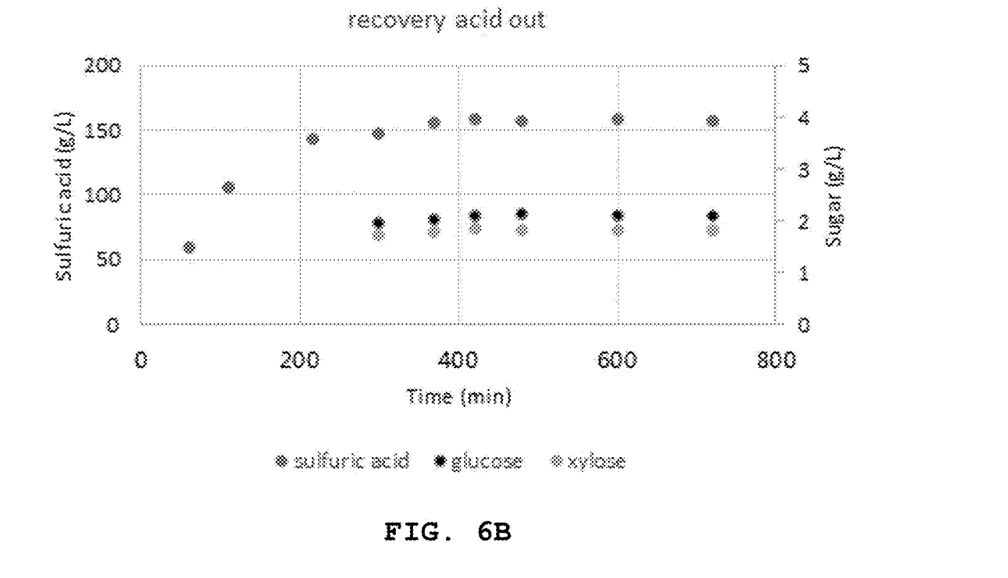

FIG. 6 shows the change in the transfer of sugars (a) and acids (b) from the model hydrolysate in a diffusion dialyzer of Control Example 1.

As shown in FIG. 6, the steady state was reached 300 minutes after the inflow of the respective solutions. The concentration of sulfuric acid in the model hydrolysate in the acid hydrolysate inflow tank was decreased from 229.65 g/L to 66.84 g/L and the recovery from the water tank was 157.14 g/L. For glucose and xylose, there was no significant change in the acid hydrolysate inflow tank from 61.35 g/L and 31.02 g/L to 61.43 g/L and 30.31 g/L and the transfer of 2.1 g/L glucose and 1.83 g/L xylose to the water tank was observed.

In order to determine the accurate material balance, the weight of the solution was measured from 300 minutes when the steady state was reached to 720 minutes. The concentration of sulfuric acid in the model hydrolysate was decreased from 101.0 g to 28.3 g and the amount of recovered sulfuric acid (water tank) was 69.7 g with an error smaller than 5%. For the sugars, glucose and xylose in the hydrolysate were decreased from 27.0 g and 13.6 g to 26.0 g and 12.8 g and the sugar loss of glucose and xylose in the water tank was 0.9 g and 0.8 g, respectively, with an error smaller than 5%.

Figure 7A:
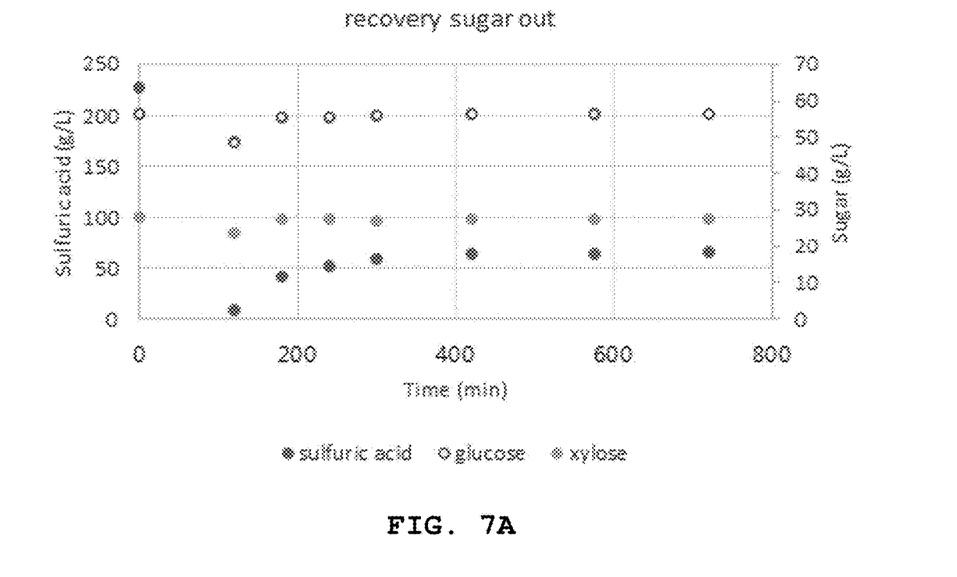
FIGS. 7A and 7B show the change in the transfer of sugars and acids from an actual hydrolysate in a diffusion dialyzer of Example 1.
Figure 7B:
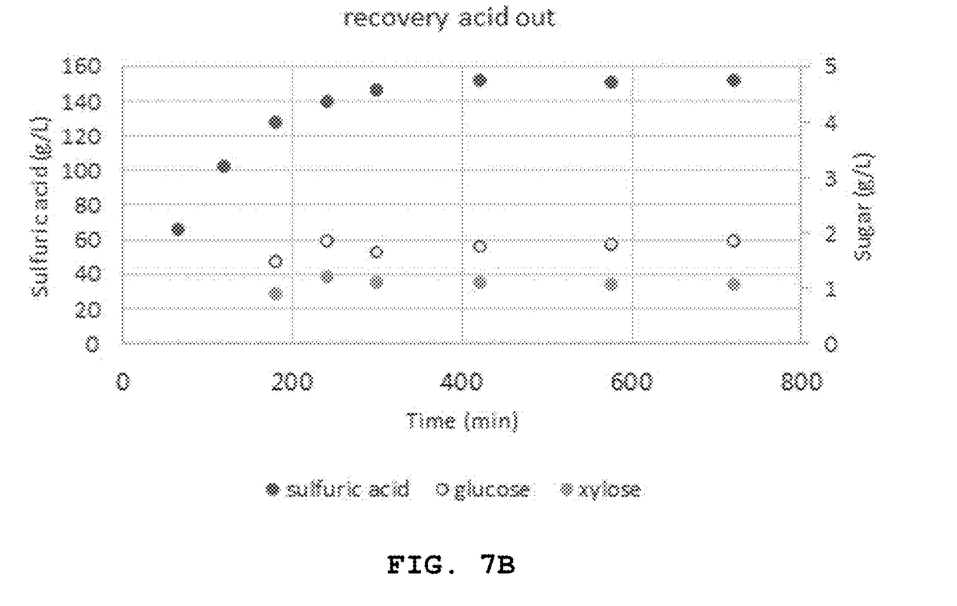
Figure 8A:
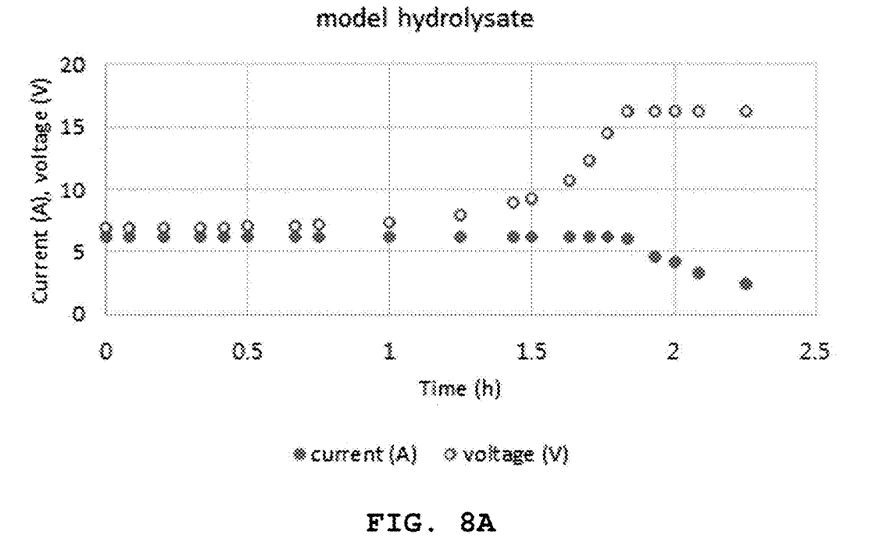
FIGS. 8A, 8B, 8C and 8D show the result of acid/sugar electrolytic separation of a model hydrolysate of Control Example 1 in an electrolyzer after diffusion dialysis depending on current and voltage and power.
Figure 8B:
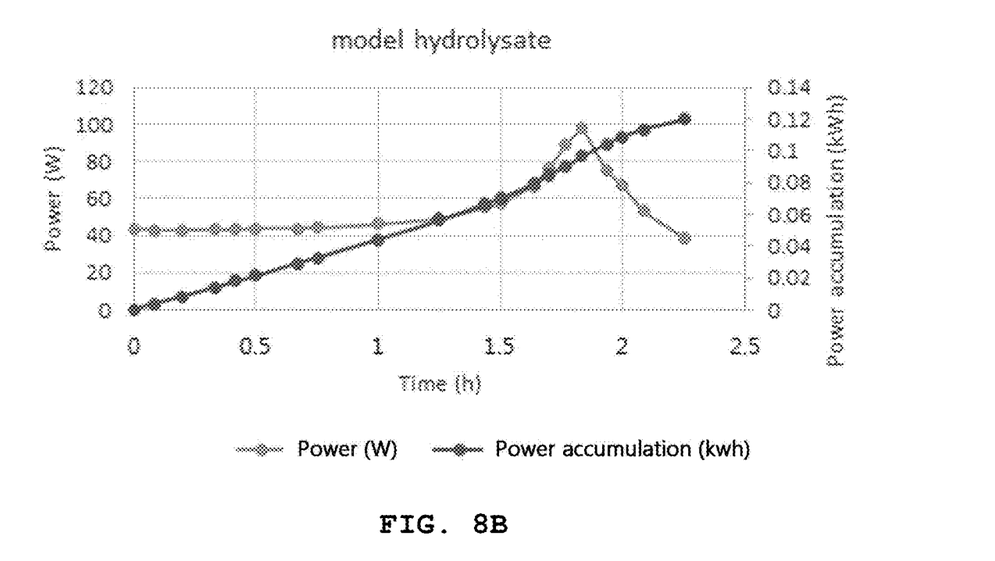
Figure 8C:
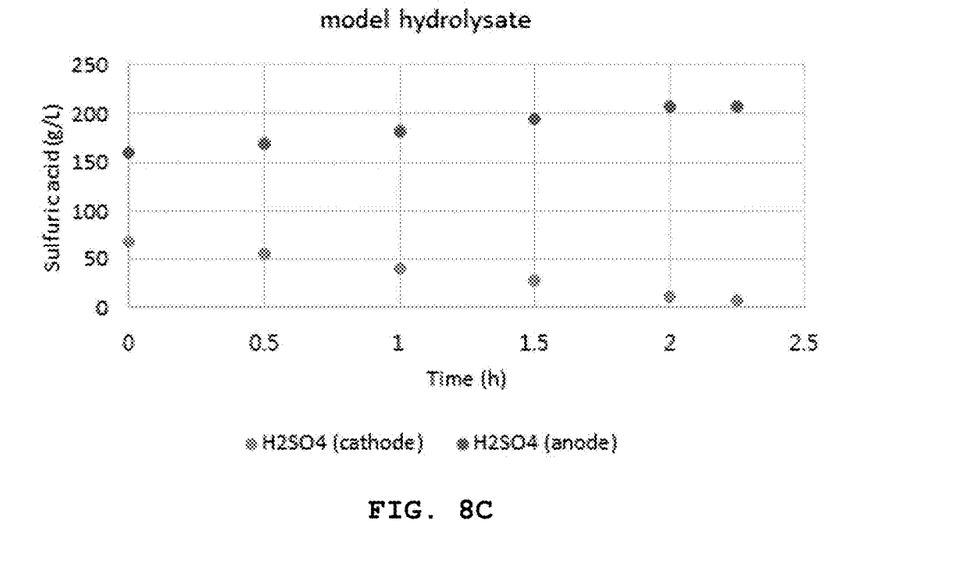
Figure 8D:
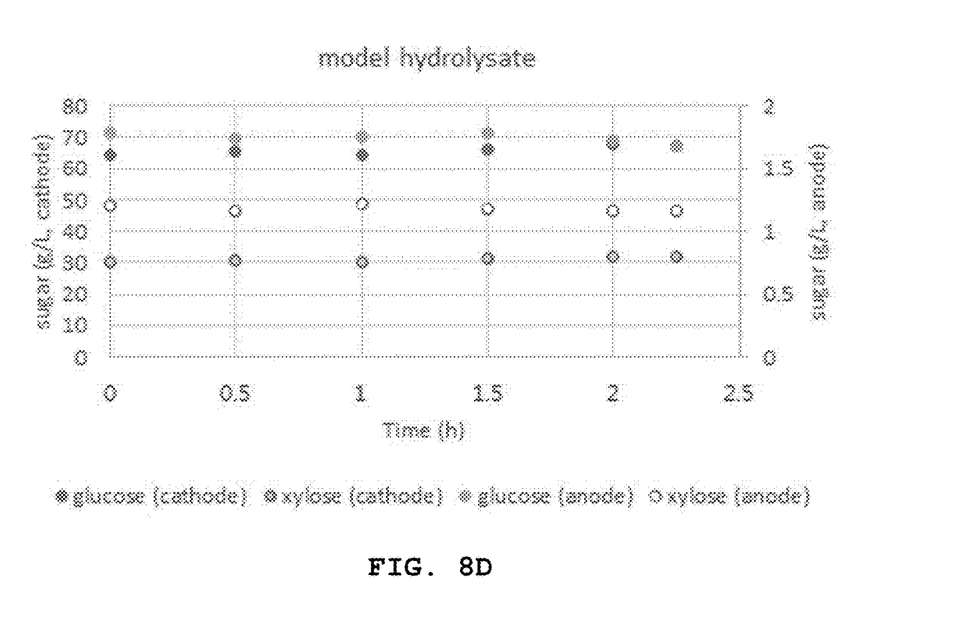
Figure 9A:
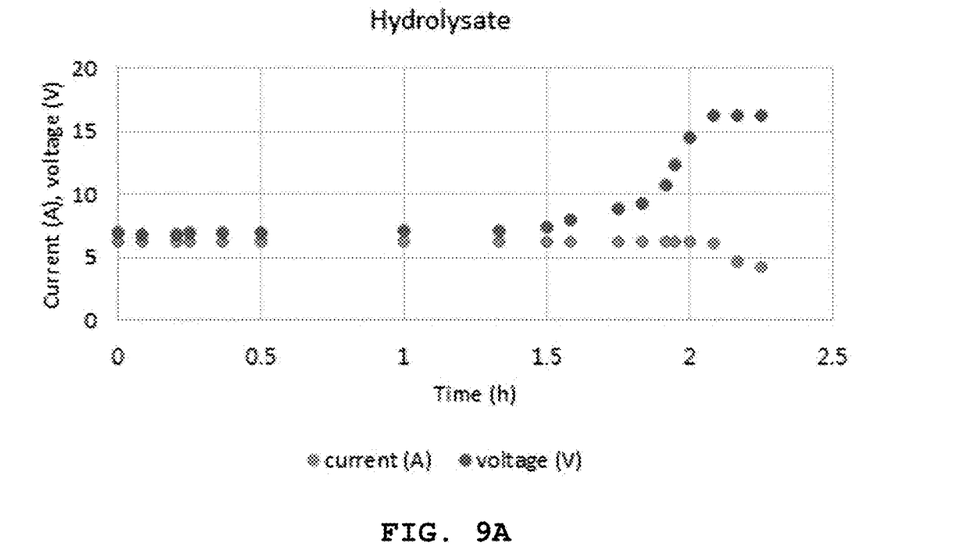
FIGS. 9A, 9B, 9C and 9D show the result of acid/sugar electrolytic separation of the actual hydrolysate of Example 1 in the electrolyzer after diffusion dialysis depending on current and voltage and power.
Figure 9B:
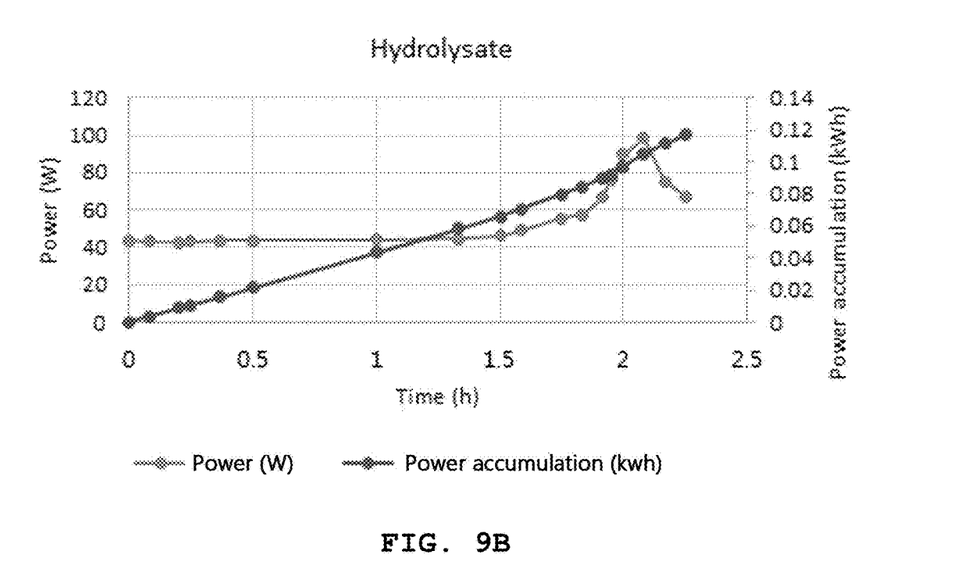
Figure 9C:
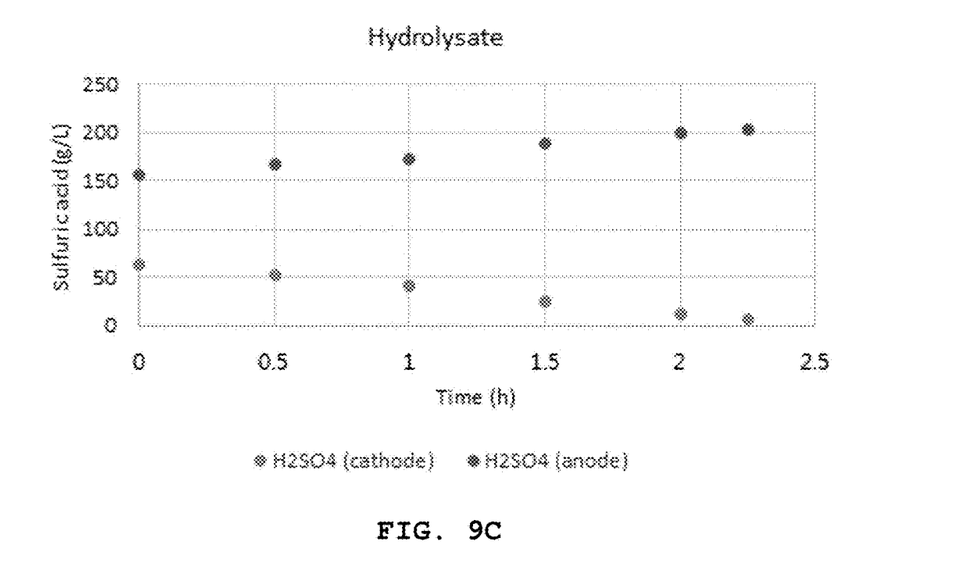
Figure 9D:
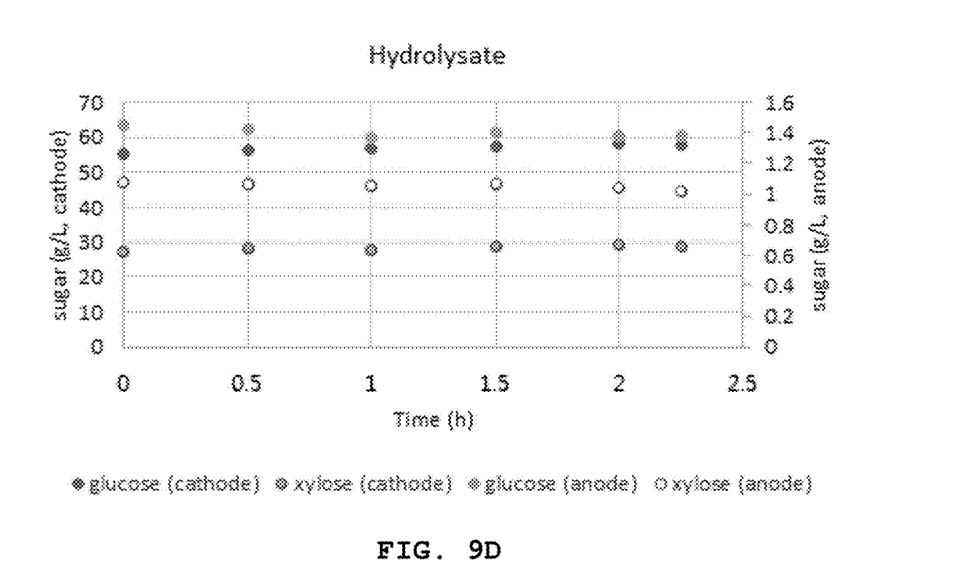

FIG. 7 shows the change in the transfer of the sugars (a) and acids (b) from the actual hydrolysate in the diffusion dialyzer of Example 1. The separation of sugars and acids through diffusion of the actual hydrolysate was conducted in the same manner as the model hydrolysate.

As seen from FIG. 7, the steady state was reached 300 minutes after the inflow of the respective solutions. The concentration of sulfuric acid in the actual hydrolysate in the acid hydrolysate inflow tank was decreased from 226.59 g/L to 62.22 g/L and the recovery from the water tank was 152.16 g/L. For glucose and xylose, there was no significant change in the acid hydrolysate inflow tank from 56.21 g/L and 27.84 g/L to 56.33 g/L and 27.33 g/L and the transfer of 1.77 g/L glucose and 1.08 g/L xylose to the water tank was observed.

In order to determine the accurate material balance, the weight of the solution was measured from 300 minutes when the steady state was reached to 720 minutes. The concentration of sulfuric acid in the actual hydrolysate was decreased from 96.3 g to 25.6 g and the amount of recovered sulfuric acid (water tank) was 66.1 g with an error smaller than 5%. For the sugars, glucose and xylose in the hydrolysate were decreased from 23.9 g and 11.8 g to 23.1 g and 11.2 g and the sugar loss of glucose and xylose in the water tank was 0.8 g and 0.5 g, respectively, with an error smaller than 5%.

It can be seen that there is no difference between the model hydrolysate and the actual hydrolysate in the efficiency of separation of sugars and acids through diffusion dialysis.

Test Example 2. Separation of Acids and Sugars Using Diffusion Dialyzers of Control Example 1 and Example 1

FIG. 8 shows the result of acid/sugar electrolytic separation (c, d) of the model hydrolysate of Control Example 1 in the electrolyzer after diffusion dialysis depending on current and voltage (a) and power (b).

As shown in FIG. 8, when sugars and acids in the model hydrolysate were separated at a current density of 25 ASD, the amount of sulfuric acid removed 2.25 hours after the completion of the reaction was 11.33 g. Because the consumed electrical energy was 119.22 Wh, the separation energy per g of sulfuric acid is 10.52 Wh/g. The electric charge consumed until the reaction was completed was 46683.59 coulomb. The theoretical transfer amount of sulfate is 0.24 gmol. When considering the actual transfer amount, the current efficiency is 47.8%.

FIG. 9 shows the result of acid/sugar electrolytic separation (c, d) of the actual hydrolysate of Example 1 in the electrolyzer after diffusion dialysis depending on current and voltage (a) and power (b).

The electrolysis experiment using the actual hydrolysate was conducted under the same condition as the model hydrolysate. The amount of sulfuric acid removed 2.25 hours after the completion of the reaction was 11.18 g. Because the consumed electrical energy was 116.81 Wh, the separation energy per g of sulfuric acid is 10.45 Wh/g. The electric charge consumed until the reaction was completed was 49101.00 coulomb. The theoretical transfer amount of sulfate is 0.25 gmol. When considering the actual transfer amount, the current efficiency is 44.8%.

This may be due to the presence of other ions that can accept electrons in the hydrolysate, the foams generated during the separation experiment, etc. However, it can be seen that the difference between the model hydrolysate and the actual hydrolysate is insignificant because the difference in efficiency is not large.

From these results, it can be seen that about 70% or more of electrical energy consumption can be reduced when the sugars and acids of the hydrolysate are separated through diffusion dialysis and electrolysis as compared to when they are separated through electrolysis only (178813.82 coulomb), suggesting that the present disclosure provides a technology capable of separating sugars and acids from a hydrolysate economically.

When diffusion dialysis was performed after electrolysis, only 50% of acids were separated in the diffusion dialysis step.

After the reaction was completed, all the sugars contained in the actual hydrolysate could be recovered and the recovery rate of sulfuric acid was as high as 90%.

[Detailed Description of Main Elements]

| | |
|---|---|
| 10: diffusion dialyzer | 11: first anion-exchange membrane |
| 12: acid hydrolysate inflow tank | 13: water tank |
| 14: mesh | |
| 20: electrolyzer | 21: second anion-exchange membrane |
| 22: anode tank | 23: cathode tank |
| 24: anode | 25: cathode |

What is claimed is:

1. A method for separating sugars and acids with reduced energy consumption, comprising:
    diffusively dialyzing a first acid hydrolysate obtained by saccharifying biomass with an acid solution, thereby preparing a second acid hydrolysate wherein the concentration of the acid solution comprised in the acid hydrolysate is decreased; and
    electrolyzing the second acid hydrolysate, thereby separating sugars from the acid solution,
    wherein the diffusion dialysis is performed using a diffusion dialyzer in which an acid hydrolysate inflow tank and a water tank are separated by an anion-exchange membrane and the reaction is performed continuously as the first acid hydrolysate is added to the acid hydrolysate inflow tank and water is added to the water tank, and
    wherein a mesh is provided at a center of the acid hydrolysate inflow tank.

2. The method for separating sugars and acids with reduced energy consumption according to claim 1, wherein the electrolysis is performed using an electrolyzer in which a cathode tank and an anode tank are separated by an anion-exchange membrane, the second acid hydrolysate wherein the concentration of the acid solution is decreased due to the diffusion dialysis is added to the cathode tank and water or an acid solution is added to the anode tank.

3. The method for separating sugars and acids with reduced energy consumption according to claim 1, wherein the concentration of the acid solution in the second acid hydrolysate is decreased by 50-80% as compared to the concentration of the acid solution in the first acid hydrolysate the due to the diffusion dialysis.

4. The method for separating sugars and acids with reduced energy consumption according to claim 1, wherein the concentration of the sugars separated by the electrolysis is 0.1-200 g/L.

5. The method for separating sugars and acids with reduced energy consumption according to claim 1, wherein the content of the final acid solution present in the sugars separated by the electrolysis is 1 wt % or lower.

6. The method for separating sugars and acids with reduced energy consumption according to claim 1, wherein the acid solution separated by the electrolysis is used directly for the saccharification of biomass.

7. The method for separating sugars and acids with reduced energy consumption according to claim 1, wherein a biofuel is produced by fermenting the sugars separated by the electrolysis.

8. The method for separating sugars and acids with reduced energy consumption according to claim 1, wherein hydrogen gas and oxygen gas are produced during the electrolysis.

9. The method for separating sugars and acids with reduced energy consumption according to claim 1, wherein the biomass is grass biomass, wood biomass, starch biomass, seaweed biomass or organic waste.

10. The method for separating sugars and acids with reduced energy consumption according to claim 1, wherein the acid solution is sulfuric acid.

11. The method for separating sugars and acids with reduced energy consumption according to claim 1, wherein the biomass is pretreated with the acid solution having an acid concentration of 1-80%.

12. The method for separating sugars and acids with reduced energy consumption according to claim 1, wherein the separated sugar is one or more selected from a group consisting of a polysaccharide selected from a group consisting of cellulose, hemicellulose, chitin, chitosan and derivatives thereof; a monosaccharide selected from a group consisting of glucose, xylose, galactose, fructose, mannose and arabinose; and a dimer or an oligomer consisting of at least one monosaccharide selected from the group consisting of glucose, xylose, galactose, fructose, mannose and arabinose.

13. A method for separating sugars and acids with reduced energy consumption, comprising:
    diffusively dialyzing a first acid hydrolysate obtained by saccharifying biomass with an acid solution, at 23-25° C. using a diffusion dialyzer equipped with an ion-exchange membrane, thereby preparing a second acid hydrolysate wherein the concentration of the acid solution comprised in the acid hydrolysate is decreased; and
    electrolyzing the second acid hydrolysate using an electrolyzer by applying a voltage of 4-6 V at 38-42° C., thereby separating sugars from the acid solution;
    wherein the diffusion dialysis is performed using the diffusion dialyzer in which an acid hydrolysate inflow tank and a water tank are separated by an anion-exchange membrane and the reaction is performed continuously as the first acid hydrolysate is added to the acid hydrolysate inflow tank and water is added to the water tank and,
    wherein a mesh is provided at a center of the acid hydrolysate inflow tank.

* * * * *